United States Patent [19]

Bartish

[11] 4,230,641

[45] Oct. 28, 1980

[54] HYDROFORMYLATION OF OLEFINS

[75] Inventor: Charles M. Bartish, Bethlehem, Pa.

[73] Assignee: Air Products and Chemicals, Inc., Allentown, Pa.

[21] Appl. No.: 853,343

[22] Filed: Nov. 21, 1977

[51] Int. Cl.³ .............................................. C07C 49/50
[52] U.S. Cl. ................................................ 568/454
[58] Field of Search ................. 260/604 HF, 632 HF; 568/909; 252/431 P, 431 R

[56] References Cited

U.S. PATENT DOCUMENTS

| | | | |
|---|---|---|---|
| 3,168,553 | 2/1965 | Slaugh | 260/604 HF |
| 3,555,098 | 1/1971 | Oliver | 260/604 HF |
| 3,647,842 | 3/1972 | Wilkes | 260/604 HF |
| 4,139,565 | 2/1979 | Unruh et al. | 260/604 HF |

*Primary Examiner*—Werren B. Lone
*Attorney, Agent, or Firm*—Russell L. Brewer; Douglas G. Glantz; E. Eugene Innis

[57] ABSTRACT

This invention relates to an improvement in a process for the hydroformylation of olefins, e.g. propylene to form saturated aldehydes. The improvement comprises reacting the olefin with carbon monoxide in the presence of a catalyst comprising a complex of a chelating phosphine ligand and a rhodium compound.

9 Claims, No Drawings

HYDROFORMYLATION OF OLEFINS

BACKGROUND OF THE INVENTION

1. Field of the Invention

This invention relates to hydroformylation reactions wherein an olefin is reacted with carbon monoxide and hydrogen to form the corresponding saturated aldehyde.

2. Description of the Prior Art

U.S. Pat. No. 3,733,362 discloses a hydroformylation reaction wherein an olefin is reacted with carbon monoxide and an alcohol, amine, water or hydrogen in the presence of a catalyst of rhodium complexed with a biphyllic phosphorus ligand. High normal/iso (n/i) ratios of aldehyde, e.g. 8:1 are shown.

U.S. Pat. Nos. 3,946,082 and 3,939,188 disclose processes for hydroformylating olefins to produce aldehydes with high ratios of normal to iso. Zerovalent rhodium-phosphine catalyst complexes of the formula $[L_2Rh]_2$ where L is a bidentate ligand are used. The disadvantage of prior art rhodium-phosphine complexes was that they become sparingly soluble in the reaction mixture and required at least a 5-10 fold excess of phosphine.

U.S. Pat. No. 3,527,809 discloses a hydroformylation process for forming aldehydes with a high normal to iso ratio by using a rhodium-phosphine complex where the phosphine ligand is present in a molar ratio of 2-100:1. Typically, molar ratios of 55:1 and temperatures from 80° to 100° C. and pressures of 80 to 250 psia are used.

U.S. Pat. No. 3,981,925 discloses the use of platinum dichloride-polydentate phosphine-stannous chloride for use in the hydroformylation of alkyl olefins.

U.S. Pat. No. 3,168,553 discloses the use of a complex of rhodium and a phosphino or arsino ligand as a catalyst for the reaction of an olefin, carbon monoxide, and a reactant having an active hydrogen and an acid dissociation content not greater than $10^{-3}$, e.g. ethanol.

SUMMARY OF THE INVENTION

This invention relates to an improvement in a hydroformylation process wherein an olefin is reacted with carbon monoxide and hydrogen in the presence of a catalyst to produce an aldehyde. The improvement resides in the employment of a complex of rhodium and a polydentate phosphorous chelating ligand of the formula $R_1R_2PAPR_3R_4$ with the molar ratio of phosphine to rhodium being from about 0.6-1.2:1 as the catalyst. When A is $(CH_2)_{5-10}$, the molar ratio of phosphine ligand to rhodium can be increased to 5:1.

Several advantages are achieved by the use of this catalyst and these advantages include:
- the ability to form a high proportion of a normal aldehyde isomer as opposed to the iso isomer, e.g. 50-80%;
- excellent reaction rates and, although generally lower than monodentate phosphine ligands at high phosphine loading, these catalysts can be used in increased quantity to bring about equivalent levels of production;
- excellent thermal stability of the catalyst system which permits separation from the aldehyde product by simple distillation without effecting decomposition of the catalyst system;
- excellent catalyst life, i.e. catalytic activity does not decrease with time and the catalysts do not form sparingly soluble carbon monoxide containing complexes; and
- the ability to eliminate the use of substantial quantities of expensive phosphine ligand to achieve catalyst stability or high reaction rates.

DESCRIPTION OF THE PREFERRED EMBODIMENT

Basically, the hydroformylation processes involve the reaction of an olefin, carbon monoxide and hydrogen in the presence of a catalyst to produce a saturated aldehyde. In these reactions the olefin generally is a $C_2$-20 and preferably a $C_3$-$C_8$ monounsaturated alpha olefin. Examples of olefins which can be reacted include ethylene, propylene, butylene, pentene, hexene, octene, decene and others conventionally used in hydroformylation processes.

Although the hydroformylation reaction is well-known, it is the catalyst complex of a rhodium compound and a chelating phosphine as described herein that provides for the advantageous results described herein.

Virtually any rhodium salts, organo rhodium compounds, and rhodium coordination compounds can be used in forming the rhodium phosphine complexes of this invention. Hence, any of the rhodium compounds used in forming prior art rhodium monodentate phosphine complexes can be used in forming the complexes of this invention. Examples of rhodium compounds which can be used in forming the rhodium-polydentate phosphine complexes of this invention, include rhodium trichloride, rhodium tribromide, rhodium chloride trihydrate, dirhodium tetracarbonyl dichloride, dirhodium tetracarbonyl dibromide, rhodium tris(triphenylphosphine) iodide, rhodium bis(triphenylphosphine) carbonyl chloride, rhodium trinitrate, and others used in the art in forming the corresponding monodentate complexes.

The phosphine ligands used in practicing the invention can be described by the formula

wherein:
- $R_1$ and $R_3$ are alkenyl groups having from 2 to 6 carbon atoms, alkyl groups having from 1 to 6 carbon atoms, hydrogen atoms, aryl groups, and substituted derivatives thereof;
- $R_2$ and $R_4$ are phenyl groups and substituted phenyl groups;
- A is a phenylene group, an alkenyl group having from 2 to 4 carbon atoms, $(CH_2)_n$ where n is from 2 to 10, and substituted derivatives thereof.

The phosphine ligand employed in the complex exhibits a substantial effect on the complex catalyst and thus on the hydroformylation reaction. In one respect the size of the bridge as described by A in the formula, influences the rate of reaction to a greater extent than it affects the selectivity to straight chain aldehydes. As a result, as the stereo chemistry of the ligand is changed, other factors regarding the reaction can be changed. For example, where A is alkenyl, phenylene or a methylene group, and n is from 2-4, the mole ratio of phosphine ligand to rhodium must be controlled to about 0.6-1.2:1, and preferably 0.9-1.1 to maintain good reaction rates. Where A is a methylene group and as n increases above 4, e.g. 5-10, the chelating phosphine ligands give faster rates with good selectivity at higher (up to 5) molar ratios of ligand.

Substituent groups on the aromatic (phenyl) ring ($R_2+R_4$) and phenyl ring ($R_1+R_3$) also can affect the performance of the catalyst in the hydroformylation reaction. Typically, electron withdrawing groups enhance the effectiveness of the phosphine ligand in promoting the reaction and electron donating groups tend to retard the rate of reaction. It is believed that the electron withdrawing group enhances reaction because it permits efficient substitution of carbon monoxide and olefin onto the rhodium atom. Examples of substituent electron withdrawing groups which are particularly effective, include chloro and fluoro groups, e.g. 4-chloro-phenyl and pentafluoro-phenyl derivatives. Where $R_1$, $R_2$, $R_3$ and $R_4$ are phenyl, though, various electron donating groups, e.g. methyl groups, can result in a satisfactory ligand.

Phenyl groups which by definition include substituted phenyl groups are preferred in the phosphine ligand because lower alkyl groups, e.g. methyl groups, tend to decrease the reactivity of the catalyst complex presumably because the binding effect between the phosphorous and rhodium atoms is too strong. For example, bis(dimethylphosphino) ethane prevents hydroformylation from occurring. On the other hand, phenyl and substituted phenyl groups permit reaction.

Examples of the phosphine complexes (abbreviations in parenthesis) that can be reacted with the rhodium compounds to produce the complexes include bis(diphenylphosphino) $C_{2-10}$ alkanes, e.g. bis(diphenylphosphino) ethane (diphos), bis(diphenylphosphino) propane (dpp), bis(diphenylphosphino) butane (dpb), bis(diphenylphosphino) ethylene, 1,2-bis(bispentafluorophenylphosphino) ethane (fos), 1,2-bis(dichlorophosphino) ethane, 1,2-bis[di(4-fluorophenyl)phosphino] ethane (4-F diphos), 1,2-bis(di-O-toly phosphino) ethane (otphos), 1,2-bis[bis(2,6-dimethylphenylphosphino)] ethane (otphos) 1,2-bis[bis(2,5-dimethylphenylphosphino)] ethane (dimotphos).

The ratio of phosphine ligand to rhodium compound (molar basis) used in the reaction broadly is from about 0.6–1.2:1 and preferably from about 0.9–1.1:1 when A is ($CH_2$) and n is 2–4, phenylene or alkylene. When the molar concentration of phosphine ligand to rhodium as metal decreases below about 0.9:1, the influence of the phosphine ligand in the hydroformylation reaction and particularly in forming the normal isomer decreases substantially; below about 0.6, the benefits are substantially insignificant. On the other hand, as the molar ratio of phosphine ligand to rhodium increases above about 1:1, e.g. 1.2:1, the reaction rate decreases substantially. However, where A is $(CH_2)_n$ and n is from 5–10 then the mole ratio can proceed to about 5:1.

The rhodium-polydentate chelating phosphine complex can be prepared in a manner identical for the preparation of the rhodium-monodentate phosphine ligands. In a typical reaction, a rhodium dicarbonyl chloride dimer and appropriate chelating phosphine, e.g. bis(diphenylphosphino) ethane are dissolved in benzene and a solution of the phosphine-benzene ligand is added to the rhodium carbonyl chloride solution. After evolution of carbon monoxide ceases, an addition of sufficient diethyl ether is made to cause cloudiness wherein the solution is cooled and the solid product recovered. Other variations of this general process for producing complexes of rhodium and phosphines appear in MAGUE AND J. MITCHENER, 8 Journal Inorganic Chemistry (1), 119–125 (1969).

Typically, the hydroformylation reaction is carried out under liquid phase conditions in a pressure vessel. Initially, the catalyst is charged and the olefin, e.g. propylene, ethylene, butylene, octene, etc. are charged followed by pressurization with hydrogen and carbon monoxide. Typically, the solvent is added to the unit in sufficient quantity to provide for intimate mixing of the catalyst with the olefin. Generally, both the catalyst and olefin should be substantially soluble in the solvent, e.g. 10 g/100 g to provide for intimate contact of the reactants. Even though polar solvents are operable and provide a medium for effecting contact between the reactants and catalysts, it has been our experience that non-polar solvents are preferred because the selectivity to the normal isomer decreases with increased solvent polarity and also the rate of reaction decreases. Preferred solvents are hydrocarbons and include toluene, xylene, benzene, hexane, isooctane, and other hydrocarbon solvents normally used in hydroformylation reactions.

The catalyst is added to the reaction medium in an amount to provide a metallic rhodium content ranging from about $1 \times 10^{-6}$ to $10^{-1}$, preferably from about $10^{-4}$ to $10^{-2}$ moles per mole of alpha-olefin feed. Although it is preferred to use lower quantities of catalyst in view of the high capital cost of rhodium metal, the stability of the catalysts enhances the operating economics.

The reaction conditions for effecting hydroformylation are those conventionally used, e.g. a temperature of from about 80°–100° C. at a pressure of from about 100 to 1,000 psi, preferably from about 300 to 700 psi. With the present catalyst system, the rate of reaction increases with increasing temperature, however, the selectivity to the normal aldehyde isomer decreases. Thus, there is a trade off in terms of rate of reaction and the proportion of normal/iso isomer that is formed. On the other hand, the selectivity to the normal isomer changes little over the pressure range of from about 100 to 1,000 psi, and typically over the 300–700 psi hydroformylation range. As might be expected, the rate of hydroformylation increases with an increase of pressure.

The following examples are provided to illustrate preferred embodiments of the invention and are not intended to restrict the scope thereof. All parts are parts by weight and all percentages are expressed as weight percentages.

EXAMPLE I

The hydroformylation of 1-octene was carried out in the following manner. Approximately 0.019 grams of $Rh_6(CO)_{16}$ was charged to a 200 ml stainless steel, glass lined pressure vessel equipped with a magnetic stirrer. After introduction of the rhodium carbonyl compound, the phosphine ligand, 12 grams of 1-octene and 21 grams of toluene were added to the pressure vessel. After stirring for about 10 minutes, the contents were preheated to a temperature of about 80° C. or within about 10° of the reaction temperature. The reactor then was sealed and flushed with 200 psi charges of a synthesis gas mixture of hydrogen and carbon monoxide and containing 50% hydrogen by volume. The vessel then was pressured to 750 psi with the synthesis gas. Continuous agitation was maintained and the reaction was observed by recording pressure drop as a function of time. The reaction was terminated at 300 psi after which the contents were analyzed for product conversion. Tables I–III show the results of various hydroformylation runs of 1-octene using various phosphine ligands, rhodium and phosphine concentrations, various phosphine-rhodium molar ratios. In the tables immediately following, L/Rh refers to the molar ratio of ligand to rhodium metal, n/i refers to the molar ratio of normal to iso isomer in percent, conversion refers to the percent of olefin converted to saturated aldehyde including both normal and iso isomer.

TABLE 1

Hydroformylation of 1-octene

| | Ligand | Conc. Rh $\times 10^4$, M | Ligand Conc. $\times 10^4$, M | L/Rh | Rate mol mol $Rh^{-1}$ $min^{-1}$ | Selectivity n/i | Temp, °C. |
|---|---|---|---|---|---|---|---|
| 1. | triphenyl phosphine (prior art) | 1.089 | 1.089 | 1 | 16.0 | 67.0 | 90 |
| | triphenyl phoshine (prior art) | 1.089 | 1.089 | 4 | 21.2 | 72.9 | 90 |
| | triphenyl phoshine (prior art) | 1.089 | 2.178 | 5 | 43.2 | 73.4 | 90 |
| | triphenyl phoshine (prior art) | 1.089 | 5.445 | 8 | 72.4 | 74.1 | 91 |
| | triphenyl phosphine (prior art) | 1.089 | 10.90 | 13 | 73.8 | 76.5 | 90 |
| | triphenyl phosphine (prior art) | 1.089 | 21.78 | 23 | 60.5 | 77.2 | 90 |
| | triphenyl phosphine (prior art) | 1.089 | 43.56 | 43 | 51.6 | 78.2 | 91 |
| 2. | bis(diphenyl phosphino) methane (dpm) | 1.089 | 0.218 | 0.2 | 7.5 | 72.7 | 91 |
| | bis(diphenyl phosphino) methane (dpm) | 1.089 | 0.435 | 0.4 | 8.7 | 72.0 | 91 |
| | bis(diphenyl phosphino) methane (dpm) | 1.089 | 0.653 | 0.6 | 9.4 | 73.8 | 91 |
| | bis(diphenyl phosphino) metnane (dpm) | 1.089 | 0.653 | 0.6 | 8.9 | 73.8 | 91 |
| 3. | bis(diphenyl phosphino) ethane (diphos) | 1.089 | 0.109 | 0.1 | 14.4 | 67.8 | 91 |
| | bis(diphenyl phosphino) ethane (diphos) | 1.089 | 0.218 | 0.2 | 28.3 | 66.9 | 91 |
| | bis(diphenyl phosphino) ethane (diphos) | 1.089 | 0.436 | 0.4 | 14.7 | 71.2 | 91 |
| | bis(diphenyl phosphino) ethane (diphos) | 1.089 | 0.652 | 0.6 | 19.5 | 73.9 | 91 |
| | bis(diphenyl phosphino) ethane (diphos) | 1.089 | 1.089 | 1.0 | 41.0 | 73.6 | 91 |
| | bis(diphenyl phosphino) | 1.089 | 2.178 | 2.0 | 16.0 | 66.1 | 91 |
| | bis(diphenyl phosphino) | 0.109 | 0.109 | 1.0 | 46.2 | 73.6 | 90 |
| 4. | bis(diphenyl phosphino) propane (dpp) | 1.089 | 0.2178 | 0.2 | 12.2 | 66.6 | 91 |
| | bis(diphenyl phosphino) propane (dpp) | 1.089 | 0.435 | 0.4 | 18.3 | 67.5 | 91 |
| | bis(diphenyl phosphino) propane (dpp) | 1.089 | 0.653 | 0.6 | 22.6 | 65.1 | 90 |
| | bis(diphenyl phosphino) propane (dpp) | 1.089 | 1.089 | 1.0 | 40.1 | 72.4 | 91 |
| | bis(diphenyl phosphino) propane (dpp) | 1.089 | 2.178 | 2.0 | 13.6 | 68.1 | 90 |

TABLE 2

| | Ligand | Conc Rh $\times 10^4$, M | Ligand Conc. $\times 10^4$, M | L/Rh | Rate mol mol $Rh^{-1}$ $min^{-1}$ | Selectivity n/i | Temp. °C. |
|---|---|---|---|---|---|---|---|
| 5. | bis(diphenyl phosphino) butane (dpb) | 1.089 | 0.109 | 0.1 | 12.1 | 68.6 | 90 |
| | bis(diphenyl phosphino) butane (dpb) | 1.089 | 0.218 | 0.2 | 14.6 | 70.4 | 90 |
| | bis(diphenyl phosphino) butane (dpb) | 1.089 | 0.435 | 0.4 | 16.2 | 73.1 | 90 |
| | bis(diphenyl phosphino) butane (dpb) | 1.089 | 0.653 | 0.6 | 22.7 | 73.2 | 90 |
| | bis(diphenyl) phosphino butane (dpb) | 1.089 | 1.089 | 1.0 | 55.1 | 72.4 | 91 |
| | bis(diphenyl phosphino) butane (dpb) | 1.089 | 2.178 | 2.0 | 8.8 | 75.5 | 90 |
| | bis(diphenyl phosphino) butane (dpb) | 1.089 | 2.178 | 2.0 | 8.8 | 74.5 | 91 |
| 6. | bis(diphenyl phosphino) pentane (dp pentane) | 1.089 | 0.218 | 0.2 | 14.0 | 69.8 | 92 |
| | bis(diphenyl phosphino) pentane (dp pentane) | 1.089 | 0.436 | 0.4 | 15.1 | 74.1 | 92 |

TABLE 2-continued

| | Ligand | Conc Rh × $10^4$, M | Ligand Conc. × $10^4$, M | L/Rh | Rate mol mol $Rh^{-1}$ $min^{-1}$ | Selectivity n/i | Temp. °C. |
|---|---|---|---|---|---|---|---|
| | bis(diphenyl phosphino) pentane (dp pentane) | 1.089 | 0.653 | 0.6 | 38.0 | 61.3 | 92 |
| | bis(diphenyl phosphino) pentane (dp pentane) | 1.089 | 1.089 | 1.0 | 43.6 | 73.5 | 92 |
| | bis(diphenyl phosphino) pentane (dp pentane) | 1.089 | 2.18 | 2.0 | 67.1 | 68.9 | 92 |
| | bis(diphenyl phosphino) pentane (dp pentane) | 1.089 | 2.18 | 2.0 | 54.2 | 73.7 | 91 |
| | bis(diphenyl phosphino) pentane (dp pentane) | 1.089 | 3.27 | 3.0 | 91.7 | 71.9 | 91 |
| | bis(diphenyl phosphino) pentane (dp pentane) | 1.089 | 5.45 | 5.0 | 98.7 | 76.4 | 91 |
| 7. | bis(diphenyl phosphino) decane (dp decane) | 1.089 | 0.218 | 0.2 | 11.8 | 72.6 | 91 |
| | bis(diphenyl phosphino) decane (dp decane) | 1.089 | 0.436 | 0.4 | 17.4 | 74.3 | 92 |
| | bis(diphenyl phosphino) decane (dp decane) | 1.089 | 0.653 | 0.6 | 21.1 | 74.0 | 91 |
| | bis(diphenyl phosphino) decane (dp decane) | 1.089 | 1.089 | 1.0 | 41.1 | 73.1 | 91 |
| | bis(diphenyl phosphino) decane (dp decane) | 1.089 | 2.18 | 2.0 | 59.8 | 75.0 | 92 |
| 8. | bis(pentafluoro phenyl-phosphino) ethane (Fos) | 1.089 | — | — | 40.9 | 61 | 89 |
| | bis(pentafluoro phenyl-phosphino) ethane (Fos) | 1.089 | 0.218 | 0.2 | 46.1 | 73.0 | 90 |
| | bis(pentafluoro phenyl-phosphino) ethane (Fos) | 1.089 | 0.435 | 0.4 | 39.0 | 74.4 | 90 |
| | bis(pentafluoro phenyl-phosphino) ethane (Fos) | 1.089 | 0.653 | 0.6 | 31.4 | 74.0 | 90 |
| | bis(pentafluoro phenyl-phosphino) ethane (Fos) | 1.089 | 1.09 | 1.0 | 19.8 | 73.5 | 90 |
| | bis(pentafluoro phenyl-phosphino) ethane (Fos) | 1.089 | 2.18 | 2.0 | 4.3 | 72.4 | 90 |

TABLE 3

| | Ligand | Conc. Rh ×$10^4$, M | Ligand Conc. × $10^4$, M | L/Rh | Rate mol mol $Rh^{-1}$ $ml^{-1}$ | Selectivity n/L | Conversion of olefin % | Temp. °C. |
|---|---|---|---|---|---|---|---|---|
| 9. | 1,2-bis(di-o-tolyl-phosphino) ethane (otphos) | 1.089 | 0.218 | 0.2 | 13.7 | 68.8 | 32.4 | 90 |
| | 1,2-bis(di-o-tolyl) phosphino) ethane (otphos) | 1.089 | 0.435 | 0.4 | 17.1 | 73.9 | 34.7 | 90 |
| | 1,2-bis(di-o-tolyl-phosphino) ethane (otphos) | 1.089 | 0.653 | 0.6 | 19.1 | 75.8 | 51.2 | 90 |
| | 1,2-bis(di-o-tolyl-phosphino) ethane (otphos) | 1.089 | 1.089 | 1.0 | 35.3 | 76.1 | 43.6 | 90 |
| | 1,2-bis(di-o-tolyl-phosphino) ethane (otphos) | 1.089 | 2.18 | 2.0 | 2.8 | 63.6 | 16.1 | 90 |
| 10. | 1,2-bis [4-fluorophenyl] phosphino] ethane (4-F-diphos) | 1.089 | 0.217 | 0.2 | 16.9 | 67.3 | 31.6 | 90 |
| | 1,2-bis [4-fluorophenyl] phosphino-9 ethane 4-F-diphos) | 1.089 | 0.435 | 0.4 | 20.9 | 73.7 | 26.2 | 90 |
| | 1,2-bis [4-fluorophenyl] phosphino-] ethane (4-F-diphos) | 1.089 | 0.653 | 0.6 | 24.7 | 74.7 | 36.3 | 90 |
| | 1,2-bis [4-fluorophenyl] phosphino-] ethane (4-F-diphos) | 1.089 | 1.089 | 1.0 | 38.4 | 73.1 | 52.4 | 90 |
| | 1,2-bis [4-fluorophenyl] phosphino-]ethane (4-F-diphos) | 1.089 | 2.17 | 2.0 | 6.2 | 51.6 | 23.0 | 90 |
| 11. | bis(diphenyl phosphino) acetylene | 1.089 | 0.218 | 0.2 | 7.9 | 74.0 | 31.6 | 90 |
| | bis(diphenyl phosphino) | | | | | | | |

TABLE 3-continued

| Ligand | Conc. Rh ×10$^4$, M | Ligand Conc. × 10$^4$, M | L/Rh | Rate mol mol Rh$^{-1}$ ml$^{-1}$ | Selectivity n/L | Conversion of olefin % | Temp. °C. |
|---|---|---|---|---|---|---|---|
| acetylene | 1.089 | 1.09 | 1.0 | 6.9 | 69.9 | 31.0 | 90 |

Abbreviations:
2. dpm
3. diphos
4. dpp
5. dpb
6. dppentane
7. dpdecane
8. fos
9. otphos
10. 4-F-diphos The results in Tables I–III show that for the hydroformylation of 1-octene about 5 moles triphenyl phosphine are required to produce the same rate of reaction as 0.6–1 moles of the chelating phosphine. Where A was (CH$_2$)$_n$ and n was 5 and 10 in the chelating phosphine, though, the rate of reaction increased substantially, e.g. to 67 and 59, respectively. On the other hand, an equivalent molar quantity of triphenyl phosphine resulted in a rate of 16 and 21.

Although good n/i ratios are obtained with both systems, the chelating phosphines are not as susceptible to thermal decomposition or conversion to sparingly soluble systems.

EXAMPLE 2

The procedure of Example I was followed except that a variety of solvents were tested to determine their effect on the hydroformylation reaction. Comparative tests were made between the chelating phosphine ligand and triphenyl phosphine ligand (PPh$_3$). Table 4 shows these results and it can be seen that the chelating phosphines resulted in better rates with 1/10th of the molar quantity of prior art phosphine. Also, selectivity to the normal isomer were superior with the chelating phosphine. On the other hand, the reaction rates were much lower than obtained in Example I. This evidence seems to show that higher rates of reaction can be obtained by using non-polar solvents.

TABLE 4

Hydroformylation of 1-octene Using Rhodium Catalysts in a Variety of Solvents.

| Conc. Rh × 10$^4$, M | Ligand Conc. × 10$^4$, M | L/Rh | Rate mol mol Rh$^{-1}$ min$^{-1}$ | Selectivity n/L | Conversion of olefin % | Ligand | Solvent |
|---|---|---|---|---|---|---|---|
| 1.089 | 10.89 | 10 | 1.76 | 39.8 | 39.8 | PPh$_3$ | 1-octanol |
| 1.089 | 10.89 | 10 | 12.3 | — | — | PPh$_3$ | 1-nonaldehyde |
| 1.089 | 10.89 | 10 | 15.6 | — | — | PPh$_3$ | diglyme |
| 1.089 | 1.089 | 1 | 12.4 | 64 | — | diphos | 1-octanol |
| 1.089 | 1.089 | 1 | 14.4 | — | — | diphos | 1-nonaldehyde |
| 1.089 | 1.089 | 1 | 12.4 | — | — | diphos | diglyme |

Conditions:
H$_2$/CO = 1.0
Initial P 750 psi
Temperature 90° C.
g octene = 12.0
g toluene = 21.0
conc. octene, M = 2.61

EXAMPLE 3

The procedure of Example 1 was repeated except that a 2.1 mole quantity of propylene was substituted for 1-octene. In addition, approximately 600 ml of toluene was used as a solvent. The phosphine ligands, concentration and temperature were varied as indicated in Table 5. Abbreviations for the ligand are used and reference can be made to Tables I–III and page 5. P(OPH)$_3$ refers to triphenyl phosphite. Selectivity refers to the percent n-aldehyde based on total aldehyde.

TABLE 5

HYDROFORMULATION OF PROPYLENE USING DIFFERENT RH-LIGAND CATALYSTS

| Rh Catalyst Conc. × 10$^{-4}$M | Ligand | Ligand Conc. × 10$^4$M | L/Rh | Temp °C. | Pres. PSI | H$_2$/CO | mole mole Rh$^{-1}$ min$^{-1}$ Rate | Selectivity |
|---|---|---|---|---|---|---|---|---|
| 1.90 | diphos | 1.94 | 1 | 80 | 500 | 2/1 | 82.4 | 52.9 |
| 1.79 | dpp | 1.78 | 1 | 80 | 500 | 2/1 | | 50.3 |
| 2.19 | dpb | 2.21 | 1 | 80 | 500 | 2/1 | 99.9 | 49.8 |
| 1.90 | dpp | 1.92 | 1 | 80 | 500 | 2/1 | 95.2 | 50.7 |
| 1.73 | dppentane | 3.43 | 2 | 80 | 500 | 2/1 | 114 | 50.8 |
| 1.99 | dphexame | 2.02 | 1 | 80 | 500 | 2/1 | 122 | 51.2 |
| 1.91 | dphexane | 3.86 | 2 | 80 | 500 | 2/1 | 136 | 50.6 |
| 1.94 | otphos | 1.94 | 1 | 80 | 500 | 2/1 | 136 | 50.6 |
| 4.80 | fos | 4.82 | 1 | 90 | 500 | 2/1 | 49.0 | 48.3 |
| 7.40 | dotphos | 7.42 | 1 | 90 | 500 | 2/1 | 30.3 | 48.1 |
| 10.0 | dotphos | 10.0 | 1 | 100 | 500 | 3/1 | 46.0 | 46.5 |
| 5.32 | dotphos | 5.31 | 1 | 120 | 500 | 3/1 | 46.9 | 45.8 |
| 4.67 | dimotphos | 4.66 | 1 | 90 | 500 | 2/1 | 96.3 | 50.1 |

TABLE 5-continued
HYDROFORMULATION OF PROPYLENE USING DIFFERENT RH-LIGAND CATALYSTS

| Rh Catalyst Conc. $\times 10^{-4}$M | Ligand | Ligand Conc. $\times 10^4$M | L/Rh | Temp °C. | Pres. PSI | $H_2$/CO | mole mole $Rh^{-1}$ min$^{-1}$ Rate | Selectivity |
|---|---|---|---|---|---|---|---|---|
| 2.13 | P(OPH)$_3$ | 110 | 50 | 80 | 130 | 1/1 | 72.3 | 68.5 |
| 2.16 | P(OPH)$_3$ | 110 | 50 | 80 | 130 | 3/1 | 34.6 | 86.9 |

Table 5 shows that good rates and selectivity are obtained with the chelating phosphine ligand. Although the prior art ligand P(OPH)$_3$ also shows good rates and selectivity, it should be noted the mole ratio of ligand to metal is quite high, i.e., 50:1. Rates fall off substantially when the ratio is 1-2:1 moles ligand to metal.

What is claimed:

1. In a hydroformylation process, wherein a $C_{2-20}$ monounsaturated alpha-olefin, carbon monoxide, and hydrogen are reacted in the presence of a catalyst comprising a complex of a phosphine ligand and rhodium to produce normal straight chain and iso saturated aldehyde isomers, at a pressure from 100-1,000 psi, the improvement for producing a high normal/iso isomer ratio and without forming sparingly soluble catalyst complexes, which comprises effecting said reaction in the presence of a catalyst comprising a complex of a rhodium compound and chelating phosphine ligand, the chelating phosphine ligand being represented by the formula: $R_1 R_2 P A P R_3 R_4$ wherein:

$R_1$ and $R_3$ are alkenyl groups having from 2 to 6 carbon atoms, alkyl groups having from 1 to 6 carbon atoms, hydrogen atoms, phenyl groups, and substituted derivatives thereof;

$R_2$ and $R_4$ are phenyl groups and substituted phenyl groups;

A is an alkenyl group having from 2 to 4 carbon atoms; and $(CH_2)_n$ wherein n is from 2 to 10 and substituted derivatives thereof; and the molar ratio of said ligand to rhodium is from about 0.6-1.2:1 provided that where A is $(CH_2)_n$ and n is from 5-10, then the molar ratio is from 1-5:1.

2. The process of claim 1 wherein A is $(CH_2)_n$.

3. The process of claim 1 wherein said olefin has from about 3-8 carbon atoms.

4. The process of claim 1 wherein $R_1$ and $R_3$ are phenyl groups.

5. The process of claim 4 wherein $R_2$ and $R_4$ are phenyl groups.

6. The process of claim 5 wherein the molar concentration of rhodium employed is from about $1 \times 10^{-6}$ to $1 \times 10^{-2}$ as metal per mole of olefin.

7. The process of claim 6 wherein the molar concentration of ligand to rhodium is from about 0.9 to 1.1:1 and n is from 2-4.

8. The process of claim 5 wherein $R_1$, $R_2$, $R_3$ and $R_4$ are substituted with substituent groups selected from the group consisting of methyl and fluoro.

9. The process of claim 5 wherein said ligand is selected from the group consisting of bis(diphenylphosphino) alkanes having from 2-10 carbon atoms, 1,2-bis(-bispentafluorophenylphosphino) ethane, 1,2-bis(di-O-tolylphosphino) ethane, and 1,2-bis[(bisdimethylphenylphosphino)] ethane.

* * * * *